United States Patent [19]

Rioux et al.

[11] 4,016,881
[45] Apr. 12, 1977

[54] INSTRUMENT FOR USE IN LAPAROSCOPIC TUBAL CAUTERIZATION

[75] Inventors: Jacques E. Rioux, Ste. Foy; Gerald Turp; François Jacques, both of Neufchatel, all of Canada

[73] Assignee: Centre de Recherche Industrielle du Quebec, Ste. Foy, Canada

[22] Filed: May 27, 1975

[21] Appl. No.: 580,752

Related U.S. Application Data

[63] Continuation-in-part of Ser. No. 378,935, July 13, 1973, Pat. No. 3,938,527.

[30] Foreign Application Priority Data

July 4, 1973  Canada ................................ 175625

[52] U.S. Cl. ........................................... 128/303.17
[51] Int. Cl.² .................... A61B 17/36; A61N 3/04
[58] Field of Search ................. 128/303.13, 303.14, 128/303.15, 303.17, 321

[56] References Cited

UNITED STATES PATENTS

| | | | |
|---|---|---|---|
| 463,785 | 11/1891 | Connable et al. | 128/321 X |
| 2,033,397 | 3/1936 | Richman | 128/303.17 |
| 2,137,710 | 11/1938 | Anderson | 128/321 |
| 3,911,923 | 10/1975 | Yoon | 128/321 X |

*Primary Examiner*—Channing L. Pace
*Attorney, Agent, or Firm*—Cushman, Darby & Cushman

[57] ABSTRACT

The instrument is used in laparoscopic tubal cauterization whereby a fallopian tube is completely blocked by coagulation and comprises: an elongated narrow sheath; an electrically insulated separator means slidably mounted in the sheath; and a pair of bipolar electrodes secured in diametrically opposite grooves extending longitudinally of the sheath. Each electrode defines at one end thereof a prong extending outwardly from one end of the sheath; the prongs are spaced from one another to define a first tube-receiving position whereby a tube may be received therebetween; the prongs may be moved to a second tube-squeezing position by slidably retracting the separator means in the sheath. The opposite end of each electrode is adapted for electrical connection to an external source of cauterizing current.

5 Claims, 12 Drawing Figures

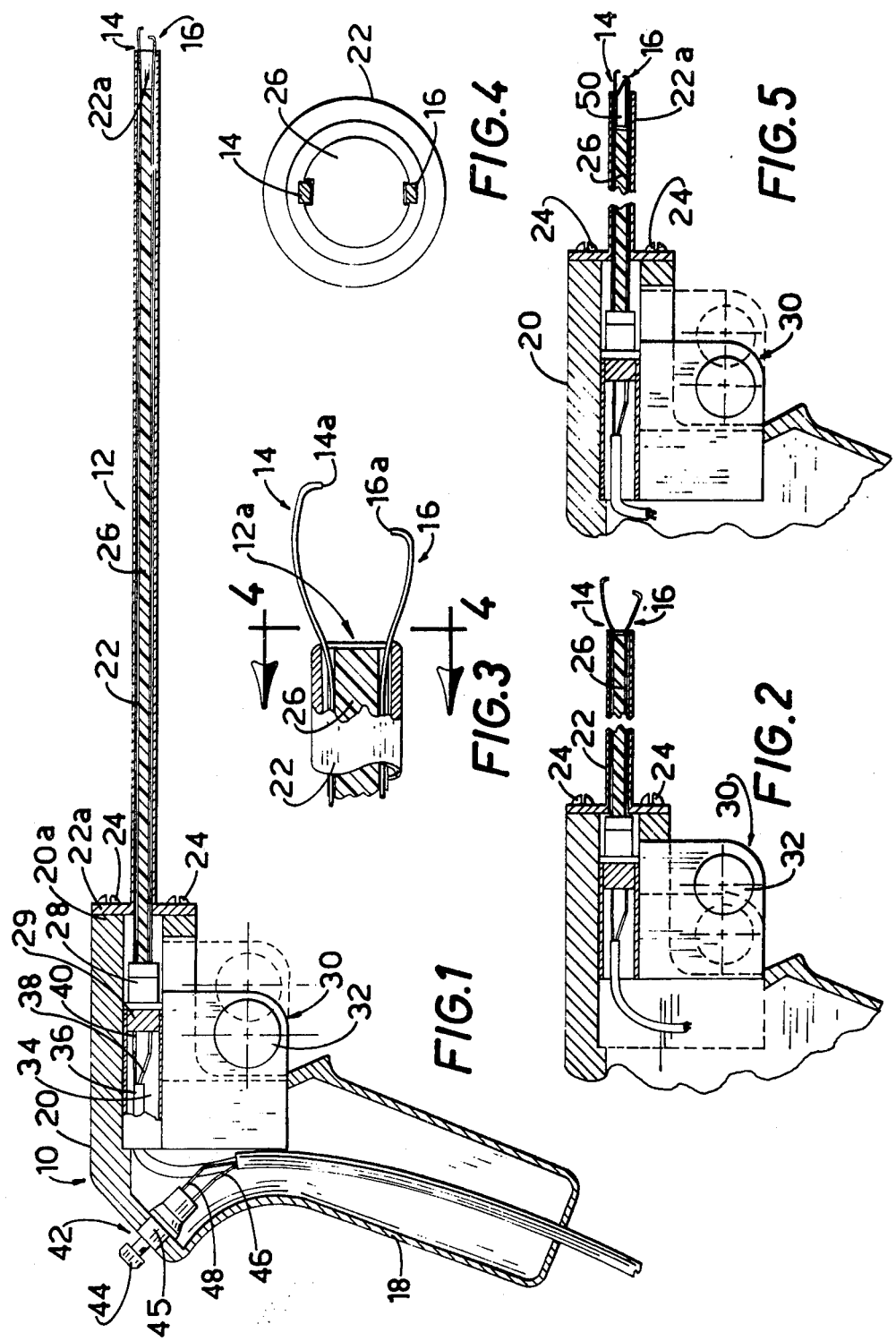

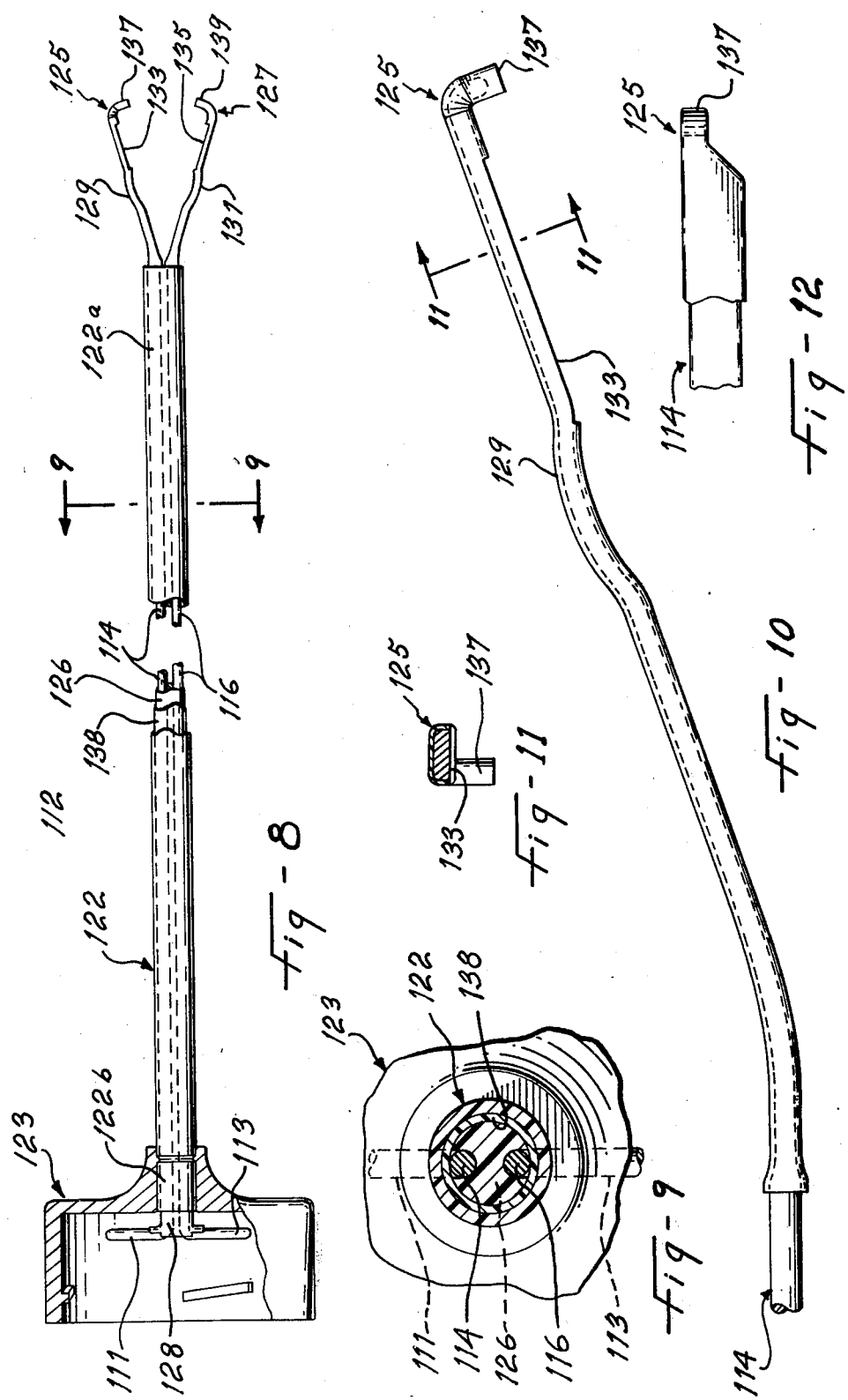

INSTRUMENT FOR USE IN LAPAROSCOPIC TUBAL CAUTERIZATION

This application is a continuation-in-part of application Ser. No. 378,935 filed July 13, 1973 now U.S. Pat. No. 3,938,527.

FIELD OF THE INVENTION

This invention relates to an instrument used in laparoscopic tubal cauterization.

Essentially, female sterilization involves cutting or blocking both fallopian tubes so that the egg released each month by the ovary cannot be reached and fertilized by the upwardly mobile sperm.

BACKGROUND OF THE INVENTION

Only recently, have new technologies emerged that promise to make female sterilization a short, outpatient procedure.

One such procedure is laparoscopic sterilization which is carried out in clinics and in hospitals under local or general anaesthesia. Using specially designed instruments, such as a laparoscope with fiber optic illumination, trained physicians can now see directly into the abdominal cavity and cut or block the fallopian tubes with only one or two small incisions to the abdomen wall.

At present, laparoscopic tubal cauterization is carried out by placing, under the bottock and back of the patient, a metal plate of fair dimensions coated with a special conductive paste. This plate is electrically connected, thus converting the whole body into one pole, while an electro-surgical instrument, having one extremity insertable in the abdominal cavity to contact the fallopian tubes, represents the other pole. The gynecologist then causes a current discharge on each tube until it becomes completely blocked by coagulation.

The popularity of laparoscopic tubal cauterization is presently being tempered by a constant flow of reports on complications. Most of these complications are due to the fact that these electro-surgical instruments work on the principle that one electrode converts the body into one pole while the specific instrument is the other pole and, since the human body is a relatively poor electrical conductor, a huge input is needed to convert the body into one pole. As a result, there is quite a spillage of electricity by the instrument in the abdominal cavity. The flow and direction of current is erratic and unpredictable and the very humid atmosphere inside the abdominal cavity and the serosity covering the organs increase the conductivity whereby production of intraabdominal sparking is made possible with secondary intestinal burning, shock, cardiac arrest and even electrocution.

Outside the body, chemical burns resulting from the substance used for the preparation of the field between the skin and the plate have been observed. Also, electrical burns from a malfunction of the unit and even actual fire burns due to the use of a flammable material (alcohol) have occurred as a result of the production of a spark outside the body.

STATEMENT OF THE INVENTION

An object of this invention is the provision of an instrument for use in laparoscopic tubal cauterization which overcomes the above-noted disadvantages plaguing present electrosurgical instruments and which will enable such operations with a minimum of risk and inconvenience to the patient.

It is an object of the present invention to provide an instrument wherein current discharge is limited and controlled thereby significantly reducing the danger of accidental electrical burns. This is achieved by providing an instrument which includes bipolar tubal forceps thereby limiting the path of the cauterizing current to the space where the tube is grasped by the forceps. Since current passes directly through the tube from one forcep to the other, coagulation is constantly under the control of the gynecologist.

The present invention therefore relates to an instrument for use in laparoscopic tubal cauterization whereby a fallopian tube is completely blocked by coagulation, which comprises:

a. an elongated narrow sheath having one open end;

b. an electrically insulated separator means slidably mounted in the sheath, said separator means having diametrically opposite electrode-receiving grooves extending longitudinally thereof; the sheath and the separator means being made of plastic material; and c. a pair of bipolar electrodes secured in the grooves, one end portion of each electrode defining a prong extending outwardly from the open end of the sheath, the prongs being spaced from one another to define a first tube-receiving position whereby a tube may be grasped between the prongs, the prongs being movable to a second tube-squeezing position in response to the separator means being slidably retracted in the sheath whereby the grasped tube is squeezed by the prongs as the prongs contact the sheath end and are closed on the tube; the opposite end of each electrode being adapted for electrical connection to an external source of cauterizing current.

Because of their bipolar function, the electrodes must be so mounted on the instrument as to avoid all contact, at any time, between them. Electro-surgical generators used in connection with this type of surgery must provide a high voltage (up to about 1200 volts peak); hence, if the electrodes should touch one another, a spark could cause injury to the patient. Furthermore, if the electrodes touch during cauterization, tube coagulation will not be satisfactorily performed since current will be short-circuited through the contacting electrodes.

On the other hand, the electrodes must be constructed to adequately grasp the tube in a first step and, then, sufficiently squeeze the tube so as to completely block the inner channel of the tube. This is achieved by bringing the two electrode extremities in close proximity to one another.

The present invention combines these seemingly divergent parameters.

Because the sheath and separator elements of the instrument are made of a plastics material, they may be manufactured and pre-sterilized at low cost and the instrument is made disposable after use.

Other objects, purposes and characteristic features of the present invention will be, in part, obvious from the accompanying drawings and, in part, pointed out as the description of the invention progresses. In describing the invention in detail, reference will be made to the accompanying drawings, in which like reference characters designate corresponding parts throughout the several views and in which:

BRIEF DESCRIPTION OF THE DRAWINGS

FIG. 1 is a cross-sectional elevation view of an instrument used for laparoscopic tubal cauterization made in accordance with the present invention;

FIG. 2 is a cross-sectional elevation view showing, in part, the instrument illustrated in FIG. 1 with the electrodes in the open position outside the probe element;

FIG. 3 is an enlarged view of one extremity of the probe element showing the electrodes in the open position;

FIG. 4 is an end cross-sectional view taken along lines 4—4 of FIG. 3;

FIG. 5 is a cross-sectional elevation view illustrating, in part, another embodiment of the present invention;

FIG. 8 is a plan view, partly broken away, of another embodiment of the probe element;

FIG. 9 is a cross-sectional view taken along lines 9—9 of FIG. 8;

FIG. 10 is an enlarged side view of one electrode extremity shown in FIG. 8;

FIG. 11 is a cross-sectional view taken along lines 11—11 of FIG. 10; and

FIG. 12 is an enlarged plan view of one electrode extremity.

Figure 6:
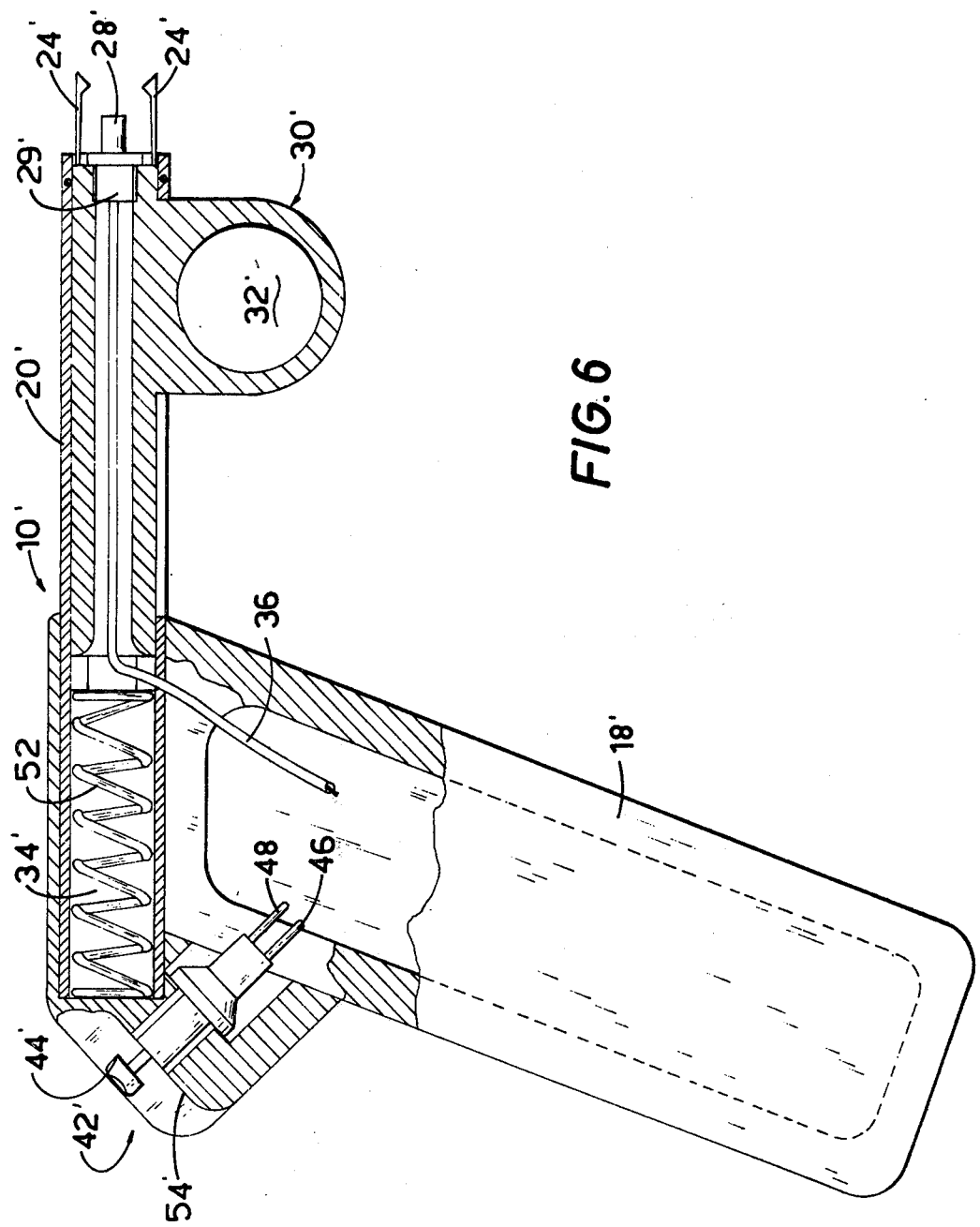
FIG. 6 is a partly cross-sectional elevation view showing another embodiment of the grip element.

Referring generally to the drawings, the instrument for use in laparoscopic tubal cauterization essentially comprises a grip member 10 and a probe element or tubal forceps 12 having one end mounted to the grip member and a pair of electrically conductive bipolar elements or electrodes 14, 16 carried in spaced relationship to one another. As it will be explained in greater detail hereinbelow, means are provided on the grip member 10 for electrically connecting the electrodes to an external power source and for generating a supply current to the electrodes.

DESCRIPTION OF ONE EMBODIMENT

Referring now more particularly to the embodiment illustrated in FIGS. 1-4, the grip member 10 is shaped in the form of a pistol that includes a hand-gripping lower portion 18 and a probe-connecting upper portion 20, each portion defining a hollow housing.

The probe element 12 is shaped in the form of a tubular sheath 22 with a flange 22a at one end thereof which is attached to a correspondingly-shaped extremity 20a of the grip portion 20 by appropriate fastening means 24. A separator element 26, made of a suitable insulating material, is slidably mounted inside sheath 22. Diametrically spaced on the separator, a pair of flat metallic wires 14 and 16 extend inside the sleeve, in parallel relationship to one another so as to avoid electrical short therebetween when current is supplied. A plug 28 is mounted to the end of the separator element 26 inside the housing of the upper portion 20 and is received in a socket 29 mounted in a recess 34 in the upper part of a slidable member 30. This member 30 has a finger-receiving opening 32 at its lower part to permit actuation thereof in the longitudinal direction of the probe element. Electrical wires 38, 40 of a cable 36 extending through housing 18 connect the socket 29 to an external power supply source (not shown). As illustrated in FIG. 2 in dotted lines, the slidable member 30 is longitudinally displaceable so that the outer ends of the electrodes, which define a pair of prongs, project outside the open end 22a of the sheath 22.

Also mounted on the grip member 20 are switch means 42 consisting of a button 44 and its connection 45 with conductors 46, 48 which are electrically connected through appropriate relay means (not shown) with the external power source so that, upon actuation of the button 44, energization of the power source causes a current supply to the electrodes.

Referring more particularly to FIGS. 2 and 3, actuation of the finger-operated slidable member 30 in the longitudinal direction of the probe element causes electrodes 14, 16 to move out of sheath 22. The material chosen for the electrodes should be sufficiently flexible so that, as they exit from the sheath end, they open up and space from one another to appropriately receive the tube to be cauterized. The tube-grasping portions of the electrodes have inwardly bent extremities or fangs 14a, 16a, the planes of which are offset relative to one another in the longitudinal axis of the separator 26 so that, as the separator is drawn in the sheath 22 as a result of member 30 being actuated, the fangs will not come in contact thereby avoiding a short circuit during cauterization.

In the embodiment illustrated in FIG. 5, the instrument is identical to that illustrated in FIGS. 1-4, except that a cutter 50 is fixedly mounted to the extremity 22a of the sheath whereby as the electrodes are drawn in the sleeve with a tube grasped therebetween, it is also possible to cut the cauterized tube.

The instrument should be made of material which is sterilized by conventional industrial sterilization processes with no deterioration of its physical and electrical characteristics.

DESCRIPTION OF USE OF THE INSTRUMENT

The use of the instrument will be best understood by describing the procedure followed during a laparoscopic tubal cauterization. The patient is given general or local anaesthesia; a small incision is made in the inferior fold of the umbilicus and a Verres cannula is then inserted into the peritoneal cavity for $CO_2$ insufflation. A sufficient quantity of $CO_2$ is insufflated while the patient is in a steep Trendelenburg position. A trocar is then introduced into the abdominal cavity and the laparoscope inserted through its sleeve.

A secondary stabbed wound is made in the mid-line or the right or left lower quadrant of the abdomen and the probe 12 is introduced under direct vision. Once received in the abdominal cavity, the electrodes are opened up by actuating the slidable member 30 to a position shown in FIG. 2. There, one tube is grasped making sure that the extremities 14a and 16a pull on the tube and do not grasp the mesosalpinx or the tubal artery which longitudinally extend behind the tube. The slidable member is then drawn in the housing thereby insuring an adequate holding engagement by the prongs on the tube. The gynecologist then actuates button 24 which causes the power source to allow a current discharge between prongs 14, 16 cauterizing that area of the tube which is grasped. The button is released once the gynecologist considers, through his laparoscope, the tube to be sufficiently coagulated. The procedure is repeated three or four times along the tube to insure adequate cauterization and complete blockage of the tube. The same procedure is repeated on the other tube. Then, the instrument is retracted and sutures are placed in the skin.

Instead of using the above described two-stabbed wound technique, the gynecologist may also use a sleeve of smaller and longer calibre which he introduces through a channel provided in the operating laparoscope. This technique does not alter the essential characteristics of the construction of the present invention.

DESCRIPTION OF OTHER EMBODIMENTS

FIG. 6 illustrates an instrument similar to the one described above but where the probe element has been omitted from the drawings for clarity purposes; however, in this embodiment a spring 52 is mounted in the upper housing of the grip member and has one end bearing against the housing of the grip member and the other end bearing against the slidable member 30'. The provision of such a spring facilitates the release of the electrodes from the cauterized tube and is especially advantageous since there is usually a tendency of the electrodes to stick to the cauterized tube.

Another feature of the embodiment illustrated in FIG. 6 consists in providing a cavity 54 in that portion of the grip member which serves to receive the switch means 42'. This cavity enables to conceal the button 44' thereby greatly reducing the chances of accidentally actuating the button.

Figure 7:
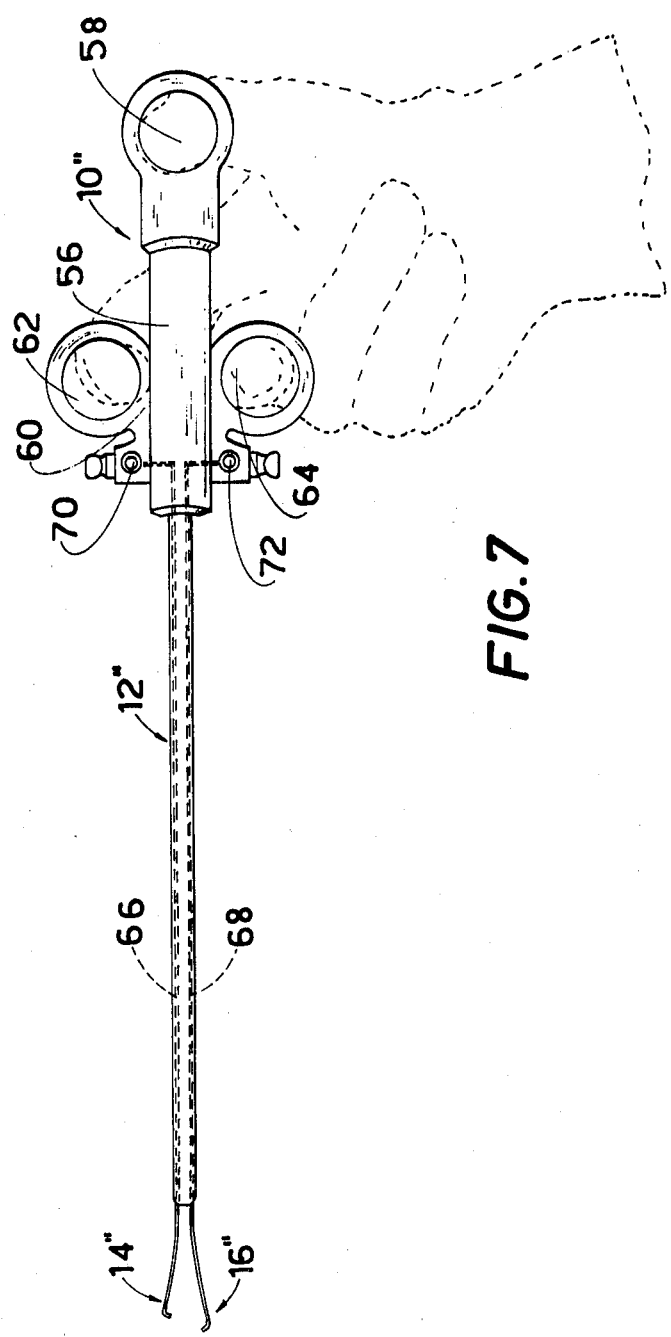
FIG. 7 is an elevation view of another embodiment of the present invention.

Referring to FIG. 7, there is shown another embodiment of the present invention in schematic form but including all the essential elements. The grip member 10" includes a first tubular member 56 one end of which has finger-receiving opening 58 and the sidewall of which includes a pair of opposite longitudinal slots (not shown) to receive therein a slidable member 60 provided with a pair of finger-receiving openings 62, 64. The probe element 12" is secured to member 56 while the electrodes 14", 16" are electrically connected to and movable with member 60. Two male extensions 70, 72 are provided on member 60 and are adapted to receive corresponding female sockets. In this case, the actuation of the power source may be carried out by a foot pedal near the gynecologist.

In another form of the invention, the electrode prongs may be coated with an anti-adherent material to prevent the electrodes from sticking on the cauterized tube.

Referring to FIGS. 8–12, there is shown another embodiment of the present invention. The probe element 112 comprises an elongated narrow sheath 122 made of a plastic material which is compatible to sterilization by gamma rays; one example of such material is nylon. The sheath has an open end 122a while its opposite end 122b is fixedly secured to a cap 123. This cap is also made of a plastic material similar to that of sheath 122. Cap 123 is adapted to be mounted to a grip member of the type which includes all of the principal elements of the grip member described above. However, such grip member would have its extremity (corresponding to extremity 20a of grip member 10 is FIG. 1) structured so as to lockingly receive cap 123.

An electrically insulated separator 126 is slidably mounted in sheath 122; the separator is cylindrically-shaped and includes two diametrically opposite grooves (see FIG. 9) extending longitudinally of the separator to receive two bipolar electrodes generally designated 114 and 116. This separator is also made of a plastic material which must be compatible to sterilization by gamma rays, such as nylon.

To further secure the electrodes 114 and 116 in their respective separator grooves, a sleeve 138 of heat shrinkable material, such as a polyvinylidene fluoride known under the trademark Kynar, surrounds the separator in a tight engagement.

A plug 128 is fixedly attached to one extremity of the separator 126 and serves to support the ends 111 and 113 of the electrodes which are bent 90° to the longitudinal axis of the separator. These extremities 111 and 113 are adapted to be received in an electrical connector (not shown) which would be mounted to the finger-actuatable mechanism slidably mounted in the grip member. Such electrical connector should be constructed to securely receive electrode extremities 111 and 113. However, since element 112 is intended to be disposed after use, this electrical connection must be constructed to allow easy disconnection of electrode extremities 111 and 113 after use.

The opposite extremities of electrodes 114 and 116 have two end portions defining flexible prongs 125 and 127 which extend outwardly from the open end 122a of the sheath. In the position shown in FIG. 8, these prongs extend about 20° from the sheath 122 to define a V-shape corresponding to a tube-receiving position whereby a fallopian tube may be grasped between the prongs. Although the main portion of electrodes 114 and 116 are shown in this embodiment as being cylindrical, it is preferable to have prongs 125 and 127 flat, of rectangular cross-sections, (see FIGS. 11 and 12) to offer a larger electrically conductive surface to the tube.

When separator 126 is slidably moved in sheath 122 (toward the left in FIG. 8), the outside walls of prongs 125 and 127 contact sheath 122 at extremity 122a causing the closing of prongs 125 and 127 on the tube which has been grasped. There results a squeezing action on the tube causing the inner channel of the fallopian tube to be blocked to provide adequate coagulation. To further assist in the squeezing of the tube, prongs 125 and 127 include outwardly curved portions 129 and 131 which, when contacting sheath 122 at extremity 122a, cause prongs 125 and 127 to be brought closer together.

To provide additional safety against accidental contacting of the prongs with surrounding organs, the prongs 125 and 127 are covered with a layer of insulating material; however, such material must offer adequate resistance to sterilization by radiation, by emersion in a sterilizing product and by gas such as ethylene oxide, and adequate resistance to heat (generated during cauterization). One product which has been found suitable is the polyvinylidene fluoride mentioned above in connection with the sheath sleeve. As shown in FIG. 10, this material is inserted over the flat portion of the electrodes in the form of a sleeve; under heat, the material shrinks to the shape of the prongs. However, one portion of this layer is scraped off to leave a non-insulated surface 133, 135 on each prong to form electrically conducting surfaces contacting the tube which is grasped between the prongs. With this arrangement, the current flow between the electrode prongs is limited to the space between the two non-insulated contact surfaces; the path of the current is thereby confined to the width of the tissue held between the prongs, thus significantly reducing the danger of accidental electrical sparks to other parts of the body.

In order to assist the tube grasping operation of the prongs, each prong extremity includes a fang 137,139 which is generally rectangular in shape and has a width smaller than the overall width of the prong. In the closed position, the fangs 137 and 139 extend in a plane which is perpendicular to a plane that includes prongs 125,127 in the closed or opened position. However, the fangs are offset to one another and disposed on either side of the said prong plane; this non-interfering of the fangs allows the prongs to be brought closer together when in the closed position. These fangs should be sufficiently rigid to enable the gynecologist, once he has grasped the tube in a secured manner, to exert a pull so as to distance the tube from surrounding body organs. Furthermore, the shape of the fangs prevents the mesosalpinx and the tubal artery, which are located behind the tube, from being damaged during the cauterizing operation.

One advantage of the present embodiment is that, the cap 123, sheath 122 and separator 126 may be made of a plastic material; it can therefore be manufactured at low cost and be made so that it is disposable after use. However, the materials which are to be selected must withstand a voltage of 1200 volts peak at frequencies up to 3 MHZ and the electrodes should be capable of carrying a high current (for example 2 amps). It is also recommended that the instrument be capable of withstanding exposure to gamma irradiation of about 2.5 MEGARAD without deterioration of its electrical and physical characteristics.

What I claim is:

1. An instrument for use in laparoscopic tubal cauterization whereby a fallopian tube is completely blocked by coagulation, comprising:
   a. an elongated narrow sheath having one open end;
   b. an electrically insulated separator means slidably mounted in said sheath, said separator means having diametrically opposite electrode-receiving grooves extending longitudinally thereof; said sheath and said separator means being made of plastic material; and
   c. a pair of bipolar electrodes secured in said grooves, one end portion of each said electrode defining a prong extending outwardly from said open end of said sheath, said prongs being spaced from one another to define a first tube-receiving position whereby a tube may be grasped between said prongs, said prongs being movable to a second tube-squeezing position in response to said separator means being slidably retracted in said sheath whereby a grasped tube is squeezed by said prongs as said prongs contact said sheath end and are closed on said tube, each said prong including inwardly bent extremities defining fangs for grasping said tube, the planes of said fangs along the longitudinal axis of said separator means being offset one relative to the other to prevent said fangs from contacting one another when in said second tube-squeezing position, and each said prong including a heat shrinkable sleeve made of insulating material, the inner face of each prong including a non-insulating portion for allowing electrical discharge to said tube during cauterization; the opposite end of each said electrode including means for electrical connection to an external source of cauterizing current.

2. An instrument as defined in claim 1, wherein each said prong includes an outwardly curved portion for engaging said sheath at the open end thereof and cause said prongs to move toward each other and squeeze said grasped tube as said curved portion is retracted in said sheath.

3. An instrument as defined in claim 1, wherein said fangs, when in said second position, extend adjacent one another in a plane perpendicular to the longitudinal axis of said electrodes.

4. An instrument as defined in claim 3, wherein said fangs are offset with respect to the longitudinal symmetry axis of said sheath; said fangs having a width smaller than the overall width of said prongs.

5. An instrument as defined in claim 4, wherein said prongs are flat, rectangular in shape.

* * * * *